United States Patent
Yu et al.

(10) Patent No.: US 10,786,488 B2
(45) Date of Patent: Sep. 29, 2020

(54) SUBSTITUTED QUINOLIZINE DERIVATIVES USEFUL AS HIV INTEGRASE INHIBITORS

(71) Applicant: MERCK SHARP & DOHME CORP., Rahway, NJ (US)

(72) Inventors: Tao Yu, Edison, NJ (US); John A. McCauley, Maple Glen, PA (US); Alan Whitehead, Scotch Plains, NJ (US); James M. Apgar, Highland Park, NJ (US); Izzat T. Raheem, Doylestown, PA (US); Guizhen Dong, Dayton, NJ (US); Sherman T. Waddell, Westfield, NJ (US); Hong Li, Edison, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/479,997

(22) PCT Filed: Jan. 23, 2018

(86) PCT No.: PCT/US2018/014761
§ 371 (c)(1),
(2) Date: Jul. 23, 2019

(87) PCT Pub. No.: WO2018/140368
PCT Pub. Date: Aug. 2, 2018

(65) Prior Publication Data
US 2019/0365727 A1   Dec. 5, 2019

Related U.S. Application Data

(60) Provisional application No. 62/450,705, filed on Jan. 26, 2017.

(51) Int. Cl.
| | |
|---|---|
| *A61K 31/4375* | (2006.01) |
| *A61K 31/427* | (2006.01) |
| *A61K 31/4402* | (2006.01) |
| *A61K 31/47* | (2006.01) |
| *A61K 31/506* | (2006.01) |
| *A61K 31/5365* | (2006.01) |
| *A61K 31/675* | (2006.01) |
| *A61K 31/7068* | (2006.01) |
| *A61K 31/7076* | (2006.01) |
| *C07D 491/147* | (2006.01) |

(52) U.S. Cl.
CPC ........ *A61K 31/4375* (2013.01); *A61K 31/427* (2013.01); *A61K 31/4402* (2013.01); *A61K 31/47* (2013.01); *A61K 31/506* (2013.01); *A61K 31/5365* (2013.01); *A61K 31/675* (2013.01); *A61K 31/7068* (2013.01); *A61K 31/7076* (2013.01); *C07D 491/147* (2013.01)

(58) Field of Classification Search
CPC .................................................. A61K 31/4375
USPC ............................................................ 546/92
See application file for complete search history.

(56) References Cited

U.S. PATENT DOCUMENTS

| | | | |
|---|---|---|---|
| 7,211,572 B2 | 5/2007 | Miyazaki et al. | |
| 7,745,459 B2 | 6/2010 | Satoh et al. | |
| 9,861,620 B2 | 1/2018 | Yu et al. | |
| 10,201,533 B2 | 2/2019 | Yu | |
| 2016/0228419 A1 | 8/2016 | Yu et al. | |

FOREIGN PATENT DOCUMENTS

| | | |
|---|---|---|
| WO | 2010011812 A1 | 1/2010 |
| WO | 2015048363 A1 | 4/2015 |
| WO | 2016154527 A1 | 9/2016 |

OTHER PUBLICATIONS

Search Report and Written Opinion for PCT/US2018/014761, dated Mar. 23, 2018, 9 pages.
Hajimahdi, Zahra et al., Progress in HIV-1 Integrase Inhibitors: A Review of their Chemical Structure Diversity, Iranian Journal of Pharmaceutical Research, 2016, 595-628, 15(4).
Johns, et al., Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744), Journal of Medicinal Chemistry, 2013, 5901-5916, 56.
Rautio, J., et al, "Prodrugs: Design and Clinical Applications", Prodrugs of Alcohols and Phenols, 2008, pp. 255-270, vol. 7, No. 3.

*Primary Examiner* — Taofiq A Solola
(74) *Attorney, Agent, or Firm* — Nicole M. Beeler; John C. Todaro

(57) ABSTRACT

The present invention relates to Substituted Quinolizine Derivatives of Formula (I): and pharmaceutically acceptable salts thereof, wherein R1 is as defined herein. The present invention also relates to compositions comprising at least one Substituted Quinolizine Derivative, and methods of using the Substituted Quinolizine Derivatives for treating or preventing HIV infection in a subject.

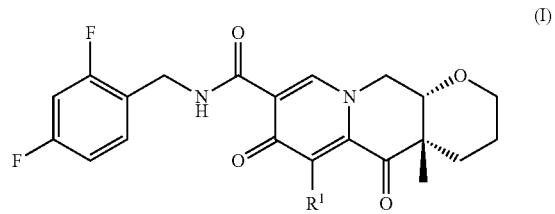

(I)

15 Claims, No Drawings

SUBSTITUTED QUINOLIZINE DERIVATIVES USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2018/014761 filed Jan. 23, 2018, which claims priority from U.S. Ser. No. 62/450,705 filed Jan. 26, 2017.

FIELD OF THE INVENTION

The present invention relates to Substituted Quinolizine Derivatives, compositions comprising at least one Substituted Quinolizine Derivative, and methods of using the Substituted Quinolizine Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

The following references may be of interest as background:

International Publication Nos. WO 11/045330 and WO 11/121105 disclose macrocyclic compounds having HIV integrase inhibitory activity.

Kinzel et al., *Tet. Letters* 2007, 48(37): pp. 6552-6555 discloses the synthesis of tetrahydropyridopyrimidones as a scaffold for HIV-1 integrase inhibitors.

Ferrara et al., *Tet. Letters* 2007, 48(37), pp. 8379-8382 discloses the synthesis of a hexahydropyrimido[1,2-a]azepine-2-carboxamide derivative useful as an HIV integrase inhibitor.

Muraglia et al., *J. Med. Chem.* 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. Nos. 7,135,467 and 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that are useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that are useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

SUMMARY OF THE INVENTION

The present invention relates to Compounds of Formula (I):

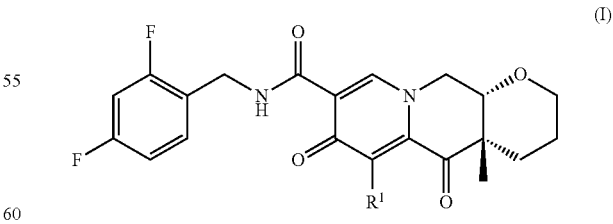

(I)

and pharmaceutically acceptable salts thereof. The compounds of Formula (I) are inhibitors of HIV integrase, and as such may be useful in the treatment, inhibition or amelioration of one or more disease states that could benefit from inhibition of HIV integrase. The compounds of Formula (I) may be useful for inhibiting HIV viral replication or replicon activity, and as such may be useful for treating or preventing HIV infection in a subject. The compounds of this invention could further be used in combination with other therapeutically effective agents, including but not limited to, other drugs useful for the treatment or prevention of HIV infection. The invention further relates to processes for preparing compounds of Formula (I), and pharmaceutical compositions which comprise compounds of Formula (I) and pharmaceutically acceptable salts thereof.

DETAILED DESCRIPTION OF THE INVENTION

The present invention relates to compounds of Formula (I):

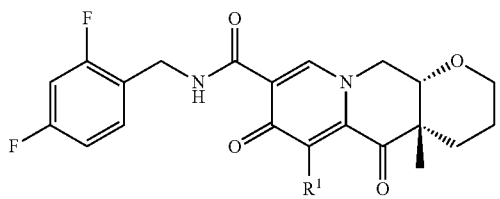

wherein:
$R^1$ is X—C(O)—Y—$R^2$;
X is O—($C_1$-$C_6$ alkylene)-O or O; and
Y is a bond, O or $NR^3$;
$R^2$ is selected from $C_1$-$C_6$ alkyl or $C_3$-$C_6$ cycloalkyl, wherein said $C_1$-$C_6$ alkyl group can be optionally substituted with one to three groups independently selected from the group consisting of halo, hydroxy, methoxy and ethoxy;
$R^3$ is selected from hydrogen or $C_1$-$C_6$ alkyl;
or a pharmaceutically acceptable salt thereof.

In an embodiment of the invention, X is O. In another embodiment of the invention, X is O—($C_1$-$C_6$ alkylene)-O.

In an embodiment of the invention, Y is O. In another embodiment of the invention, Y is a bond. In another embodiment of the invention, Y is $NR^3$.

In an embodiment of the invention, $R^1$ is selected from:

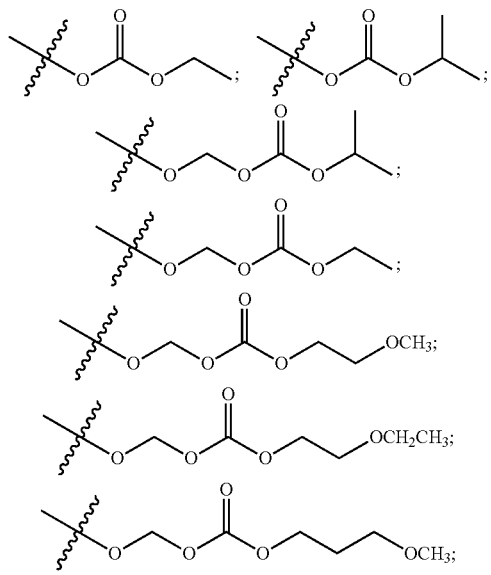

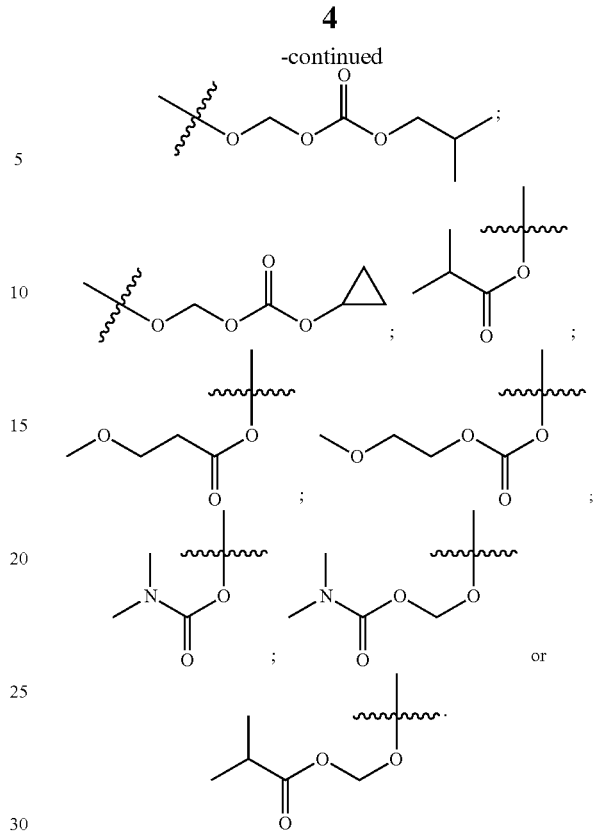

In an embodiment of the invention, $R^2$ is selected from the group consisting of methyl; ethyl, which is optionally substituted with methoxy or ethoxy; propyl, which is optionally substituted with methoxy; or cyclopropyl.

In an embodiment of the invention, $R^3$ is methyl. In another embodiment of the invention, $R^3$ is hydrogen.

In another embodiment, the compounds of Formula (I) are in substantially purified form.

Other embodiments of the present invention include the following:

(a) A pharmaceutical composition comprising an effective amount of a compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, CCR5 co-receptor antagonists, nucleoside reverse transcriptase inhibitors and non-nucleoside reverse-transcriptase inhibitors.

(d) A pharmaceutical combination that is (i) a compound of Formula (I) and (ii) a second therapeutic agent selected from the group consisting of HIV antiviral agents, immunomodulators, and anti-infective agents; wherein the compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, CCR5 co-receptor antagonists, nucleoside reverse transcriptase inhibitors and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a compound of Formula (I).

(h) The method of (g), wherein the compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, CCR5 co-receptor antagonists, nucleoside reverse transcriptase inhibitors and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The compounds of Formula (I) may be referred to herein by chemical structure and/or by chemical name. In the instance that both the structure and the name of a compound of Formula (I) are provided and a discrepancy is found to exist between the chemical structure and the corresponding chemical name, it is understood that the chemical structure will predominate.

The compounds of Formula (I) (also referred to herein as the "Substituted Quinolizine Derivatives") and pharmaceutically acceptable salts thereof can be useful, for example, for inhibiting HIV viral replication or replicon activity, and for treating or preventing HIV infection in a subject.

As illustrated below, the $R^1$ group of the compounds of Formula (I) can be hydrolyzed under physiological conditions to provide the corresponding hydroxy compounds.

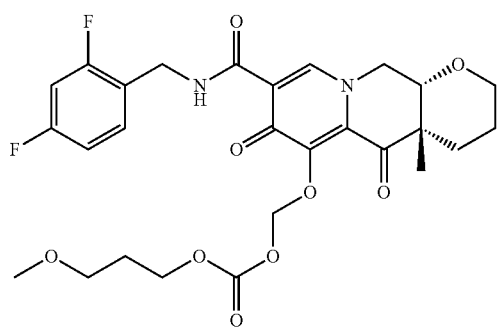 [SMILES: COCCCOC(=O)OCOc1c2n(cc(C(=O)NCc3ccc(F)cc3F)c1=O)C[C@@H]1OCCC[C@]1(C)C2=O]

Accordingly, the present invention provides methods for treating or preventing HIV infection in a subject, comprising administering to the subject an effective amount of at least one Substituted Quinolizine Derivative.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Substituted Quinolizine Derivatives and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl" as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkylene" as used herein, refers to an aliphatic hydrocarbon group having two of its hydrogen atoms from different carbons replaced with a bond. An alkylene group may be straight or branched and contain from about 1 to about 20 carbon atoms. In one embodiment, an alkylene group contains from about 1 to about 12 carbon atoms. In different embodiments, an alkylene group contains from 1 to 6 carbon atoms ($C_1$-$C_6$ alkylene) or from about 1 to about 4 carbon atoms ($C_1$-$C_4$ alkylene). Non-limiting examples of alkylene groups include methylene, ethylene, propylene, isopropylene, butylene, isobutylene, pentylene, etc. In one embodiment, an alkylene group is linear. In another embodiment, an alkyl group is branchedene. Unless otherwise indicated, an alkylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. The term "3 to 7-membered cycloalkyl" refers to a cycloalkyl group having from 3 to 7 ring carbon atoms. Unless otherwise indicated, a cycloalkyl group is unsubstituted. The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^2$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

It will be understood that, as used herein, references to the compounds of structural Formula (I) are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzyl ethylenediamine, diethylamine, 2-diethyl aminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention may form an acid addition salt and a salt with a base at the same time according to the type of substituent of the side chain.

If the compounds of Formula (I) simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that enantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packing properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Polymorphic forms of the Substituted Quinolizine Derivatives, and of the salts, solvates, hydrates and esters of the Substituted Quinolizine Derivatives, are intended to be included in the present invention.

Uses of the Substituted Quinolizine Derivatives

The Substituted Quinolizine Derivatives are useful in human and veterinary medicine for treating or preventing HIV infection in a subject. In one embodiment, the Substituted Quinolizine Derivatives can be inhibitors of HIV viral replication. In a specific embodiment, the Substituted Quinolizine Derivatives are inhibitors of HIV-1. Accordingly, the Substituted Quinolizine Derivatives are useful for treating HIV infections and AIDS. In accordance with the invention, the Substituted Quinolizine Derivatives can be administered to a subject in need of treatment or prevention of HIV infection.

Accordingly, in one embodiment, the invention provides methods for treating HIV infection in a subject comprising administering to the subject an effective amount of at least one Substituted Quinolizine Derivatives or a pharmaceutically acceptable salt thereof. In a specific embodiment, the present invention provides methods for treating AIDS in a subject comprising administering to the subject an effective amount of at least one Substituted Quinolizine Derivatives or a pharmaceutically acceptable salt thereof.

Treatment or Prevention of HIV Infection

The Substituted Quinolizine Derivatives are useful in the inhibition of HIV, the treatment of HIV infection and/or reduction of the likelihood or severity of symptoms of HIV infection and the inhibition of HIV viral replication and/or HIV viral production in a cell-based system. For example, the Substituted Quinolizine Derivatives are useful in treating infection by HIV after suspected past exposure to HIV by such means as blood transfusion, exchange of body fluids, bites, accidental needle stick, or exposure to subject blood during surgery or other medical procedures.

In one embodiment, the HIV infection has progressed to AIDS.

Accordingly, in one embodiment, the invention provides methods for treating HIV infection in a subject, the methods comprising administering to the subject an effective amount of at least one Substituted Quinolizine Derivatives or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject.

The Substituted Quinolizine Derivatives are also useful in the preparation and execution of screening assays for antiviral compounds. For example the Substituted Quinolizine Derivatives are useful for identifying resistant HIV cell lines harboring mutations, which are excellent screening tools for more powerful antiviral compounds. Furthermore, the Substituted Quinolizine Derivatives are useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not Substituted Quinolizine Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Substituted Quinolizine Derivatives (which may include two or more different Substituted Quinolizine Derivatives), or a pharmaceutically acceptable salt thereof, and (ii) at least one additional therapeutic agent that is other than a Substituted Quinolizine Derivatives, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Substituted Quinolizine Derivatives and an additional therapeutic agent may be present in fixed amounts (dosage amounts) in a single dosage unit (e.g., a capsule, a tablet and the like).

In one embodiment, the at least one Substituted Quinolizine Derivatives is administered during a time when the additional therapeutic agent(s) exert their prophylactic or therapeutic effect, or vice versa.

In another embodiment, the at least one Substituted Quinolizine Derivatives and the additional therapeutic agent(s) are administered in doses commonly employed when such agents are used as monotherapy for treating a viral infection.

In another embodiment, the at least one Substituted Quinolizine Derivatives and the additional therapeutic agent(s) are administered in doses lower than the doses commonly employed when such agents are used as monotherapy for treating a viral infection.

In still another embodiment, the at least one Substituted Quinolizine Derivatives and the additional therapeutic agent(s) act synergistically and are administered in doses lower than the doses commonly employed when such agents are used as monotherapy for treating a viral infection.

In one embodiment, the at least one Substituted Quinolizine Derivatives and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Substituted Quinolizine Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Substituted Quinolizine Derivatives and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| doravirine | nnRTI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |

TABLE A-continued

| Name | Type |
|---|---|
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, doravirine, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is doravirine.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, doravirine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, doravirine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, $57^{th}$ edition (2003) through the $70^{th}$ edition (2016), Thomson PDR, and the like. The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Substituted Quinolizine Derivatives(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Substituted Quinolizine Derivatives can be administered as a component of a composition that comprises a pharmaceutically acceptable carrier or vehicle. The present invention provides pharmaceutical compositions comprising an effective amount of at least one Substituted Quinolizine Derivatives and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Substituted Quinolizine Derivatives are administered orally.

In another embodiment, the one or more Substituted Quinolizine Derivatives are administered intravenously.

In one embodiment, a pharmaceutical preparation comprising at least one Substituted Quinolizine Derivatives is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Substituted Quinolizine Derivatives(s) by weight or volume. In various embodiments, the present compositions can contain, in one embodiment, from about 1% to about 70% or from about 5% to about 60% of the Substituted Quinolizine Derivatives(s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Substituted Quinolizine Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) at least one Substituted Quinolizine Derivatives or a pharmaceutically acceptable salt thereof; (ii) one or more additional therapeutic agents that are not a Substituted Quinolizine Derivatives; and (iii) a pharmaceutically acceptable carrier, wherein the amounts in the composition are together effective to treat HIV infection.

Kits

In one aspect, the present invention provides a kit comprising a therapeutically effective amount of at least one Substituted Quinolizine Derivatives, or a pharmaceutically acceptable salt of said compound and a pharmaceutically acceptable carrier, vehicle or diluent.

In another aspect the present invention provides a kit comprising an amount of at least one Substituted Quinolizine Derivatives, or a pharmaceutically acceptable salt of said compound and an amount of at least one additional therapeutic agent listed above, wherein the amounts of the two or more active ingredients result in a desired therapeutic effect. In one embodiment, the one or more Substituted Quinolizine Derivatives and the one or more additional therapeutic agents are provided in the same container. In one embodiment, the one or more Substituted Quinolizine Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

Non-limiting examples of the Compounds of Formula (I) include compounds 1-14 as set forth below, and pharmaceutically acceptable salts thereof.

The following abbreviations are used below and have the following meanings: 18-crown-6 is 1,4,7,10,13,16-hexaoxacyclooctadecane; DMSO is dimethyl sulfoxide; EtOAc is ethyl acetate; h is hour; HPLC is high-pressure liquid chromatography; LCMS is liquid chromatography-mass spectrometry; MeOH is methanol; min. is minute; MS is mass spectroscopy; MTBE is methyl tert-butyl ether; MPLC is medium pressure liquid chromatography; NMR is nuclear magnetic resonance spectroscopy; SFC is supercritical fluid chromatography; TFA is trifluoroacetic acid; TLC is thin-layer chromatography; Ts is tosyl or 4-toluenesulfonyl; THF is tetrahydrofuran; Hz is hertz; δ is chemical shift; d is doublet; dd is doublet of doublets; MHz is megahertz.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Intermediates and Examples below. Alternative synthetic pathways and analogous structures will be apparent to those skilled in the art of organic synthesis.

General Methods

Compounds of the present invention may be prepared using conventional techniques or according to the methodology outlined in the following general synthetic schemes.

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed with electrospray ionization in positive ion detection mode. $^1$H NMR spectra were recorded on Varian or Bruker instruments at 400-500 MHz. Concentration of solutions was carried out on a rotary evaporator under reduced pressure or by lyophilization. Flash chromatography was performed on pre-packed silica gel columns using a commercial MPLC system.

Intermediates

Preparation of Intermediate Compound Int-1

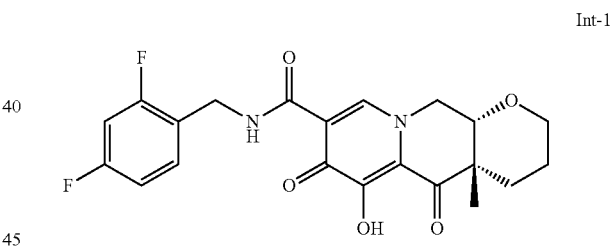

Int-1

Compound Int-1 was prepared using the method described in U.S. Patent Publication No. WO2015048363 (A1).

Preparation of Intermediate Compound Int-2

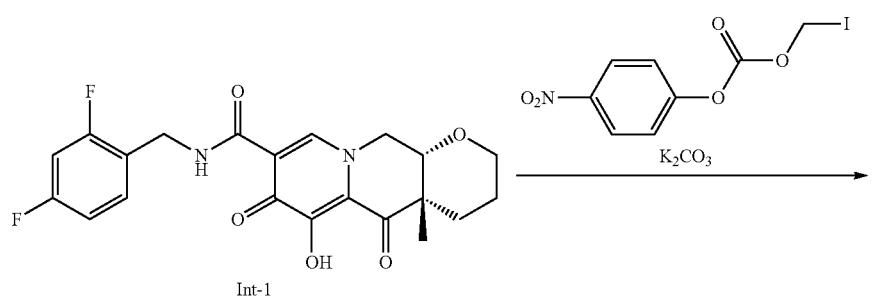

Int-1

-continued

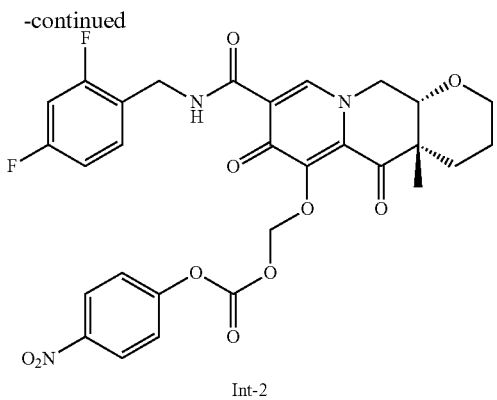

Int-2

To a solution of compound Int-1 (115.8 mg, 0.277 mmol) in 2.8 mL of acetonitrile, was added potassium carbonate (132 mg, 0.955 mmol) followed by iodomethyl (4-nitrophenyl) carbonate (268 mg, 0.830 mmol). The reaction mixture was stirred at 55° C. for 1 h. It was cooled to room temperature, and diluted with 20 mL of dichloromethane. The mixture was filtered and the filtrate was concentrated. The residue was diluted in 50 mL of dicholromethane. This was washed with 50 mL of water. The organic was concentrated. The residue was purified by ISCO, normal phase HP Gold silica gel (40 g), eluting with dicholromethane/MeOH (100% dicholromethane for 2 min; gradient to 5% MeOH in dicholromethane over 12 min, isocratic for 5 min) to give compound Int-2. LCMS M+1=614.3.

mmol). The reaction mixture was stirred at room temperature for 30 min. The resulting mixture was filtered, and the filtrate was concentrated under vacuum. The residue was purified by ISCO, normal phase HP Gold silica gel (80 g), eluting with hexanes/EtOAc (100% of hexanes for 5 min; gradient from 70 to 100% EtOAc in hexanes over 20 min, isocratic for 5 min) to give compound 1.

Compound 1: $^1$H NMR (400 MHz, CDCl$_3$) δ: 10.50-10.35 (brs, 1H), 8.49 (s, 1H), 7.38-7.32 (m, 1H), 6.85-6.76 (m, 2H), 4.67-4.57 (m, 2H), 4.53 (dd, J=13.6, 2.1 Hz, 1H), 4.38 (q, J=7.1 Hz, 2H), 4.23 (dd, J=13.6, 2.4 Hz, 1H), 3.98 (dd, J=11.3, 4.7 Hz, 1H), 3.80 (dd, J=2.3, 2.2 Hz, 1H), 3.53-3.45 (m, 1H), 2.60-2.53 (m, 1H), 1.52-1.36 (m, 6H), 1.21 (s, 3H). LCMS M+1=491.1.

EXAMPLES

Example 1

Preparation of Compound 1

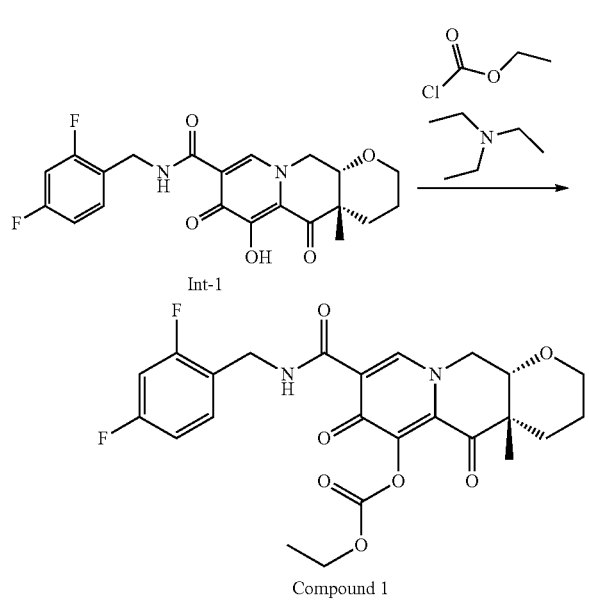

Compound 1

Example 2

Preparation of Compound 2

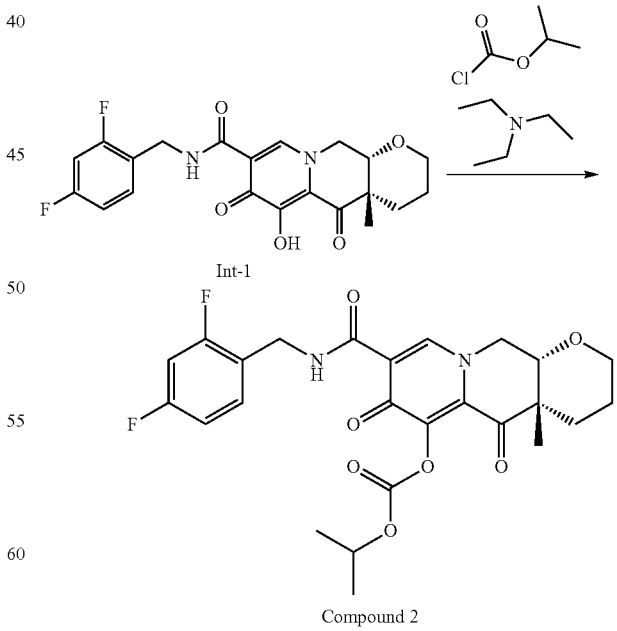

Compound 2

To a solution of compound Int-1 (1.5 g, 3.59 mmol) in 36 mL of THF, was added triethylamine (2.499 ml, 17.93 mmol) followed by ethyl chloroformate (1.033 ml, 10.76

To a solution of compound Int-1 (1.5 g, 3.59 mmol) in 36 mL of THF, was added triethylamine (2.499 ml, 17.93 mmol) followed by isopropyl carbonochloridate (1M in Toluene) (10.76 mL, 10.76 mmol). The reaction mixture was stirred at room temperature for 30 min. The resulting mixture was filtered, and the filtrate was concentrated under vacuum. The residue was purified by ISCO, normal phase HP Gold silica gel (80 g), eluting with hexanes/EtOAc (100% of hexanes for 5 min; gradient from 70 to 100% EtOAc in hexanes over 20 min, isocratic for 5 min) to give compound 2.

Compound 2: $^1$H NMR (400 MHz, CDCl$_3$) δ: 10.32-10.20 (brs, 1H), 8.45 (s, 1H), 7.38-7.32 (m, 1H), 6.83-6.72 (m, 2H), 5.05-4.95 (m, 1H), 4.66-4.55 (m, 2H), 4.51 (dd, J=13.6, 2.1 Hz, 1H), 4.23 (dd, J=13.6, 2.3 Hz, 1H), 3.98-3.92 (m, 1H), 3.81-3.79 (brs, 1H), 3.51-3.42 (m, 1H), 2.58-2.51 (m, 1H), 1.52-1.32 (m, 9H), 1.20 (s, 3H). LCMS M+1=505.1.

Example 3

Preparation of Compound 3

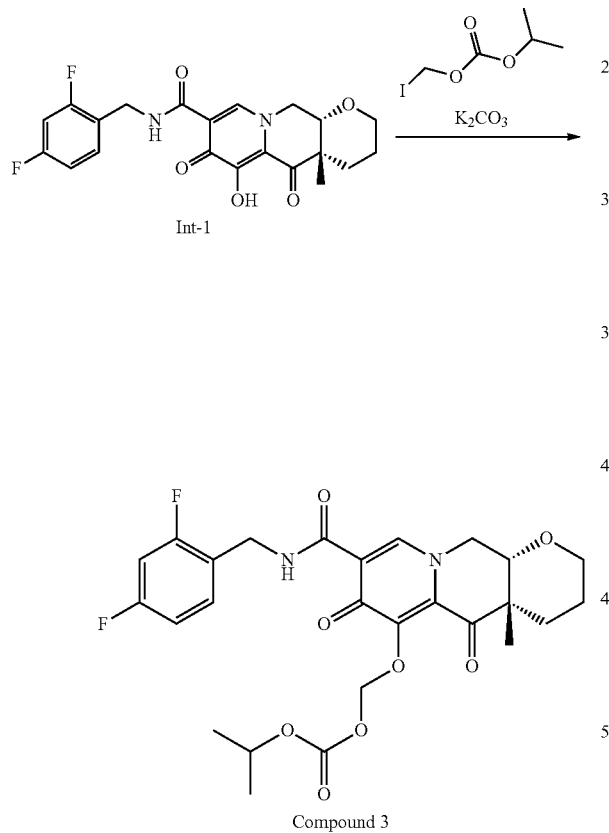

Compound 3

To a solution of compound Int-1 (2 g, 4.78 mmol) in 48 mL of acetonitrile, was added potassium carbonate (2.279 g, 16.49 mmol) followed by iodomethyl isopropyl carbonate (4.37 g, 14.34 mmol). The reaction mixture was stirred at 55° C. for 1 h. The resulting mixture was cooled to room temperature, and diluted with 150 mL of dichloromethane. The mixture was filtered and the filtrate was concentrated. The residue was purified by ISCO, normal phase HP Gold silica gel (80 g), eluting with dichloromethane/MeOH (100% of dichloromethane for 5 min; gradient from 0 to 5% MeOH in dichloromethane over 25 min, isocratic for 10 min) to give compound 3.

Compound 3: $^1$H NMR (400 MHz, CDCl$_3$) δ: 10.33-10.28 (brs, 1H), 8.41 (s, 1H), 7.38-7.33 (m, 1H), 6.86-6.77 (m, 2H), 5.92 (d, J=6.5 Hz, 1H), 5.90 (d, J=6.5 Hz, 1H), 4.98-4.90 (m, 1H), 4.67-4.58 (m, 2H), 4.49 (dd, J=13.6, 2.1 Hz, 1H), 4.19 (dd, J=13.7, 2.6 Hz, 1H), 3.96 (dd, J=11.4, 4.9 Hz, 1H), 3.77 (t, J=2.3 Hz, 1H), 3.52-3.43 (m, 1H), 2.57-2.51 (m, 1H), 1.71-1.60 (m, 1H), 1.50-1.30 (m, 8H), 1.19 (s, 3H). LCMS M+1=535.1.

Example 4

Preparation of Compound 4

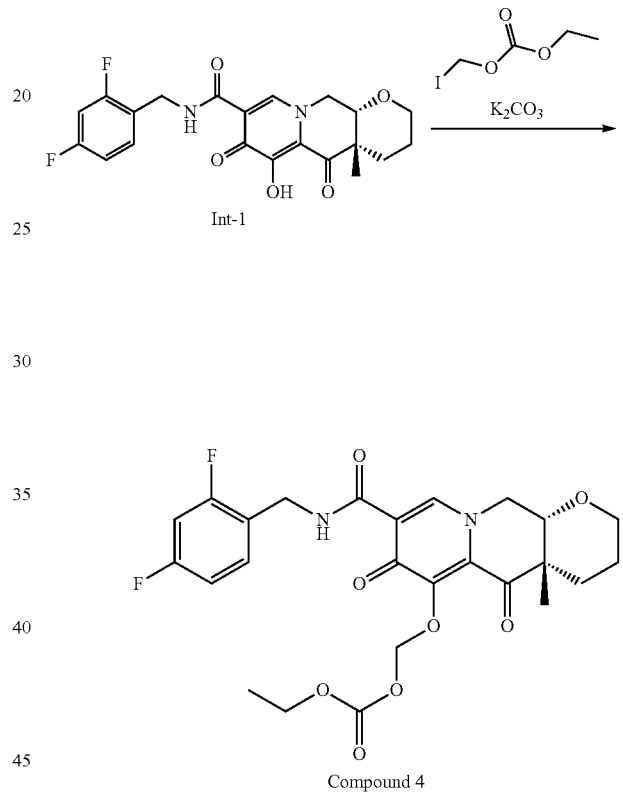

Compound 4

A mixture of compound Int-1 (2.500 g, 5.98 mmol), ethyl (iodomethyl) carbonate (4.12 g, 17.93 mmol) and potassium carbonate (2.89 g, 20.91 mmol) in 60 mL of acetonitrile was heated at 55° C. for 1 h. The reaction was cooled to room temperature and diluted with 150 mL of dichloromethane. The mixture was filtered and the filtration was concentrated. The residue was diluted in 100 mL of dichloromethane and washed with 100 mL of water. The organic phase was dried with Na$_2$SO$_4$ and concentrated. The residue was purified with ISCO (loaded onto a 80 g gold cartridge, eluting with 0~100% EtOAc in hexanes, the peak was collected at 100% EtOAc to provide compound 4.

Compound 4: $^1$H NMR (400 MHz, CDCl$_3$) δ: 10.36-10.30 (brs, 1H), 8.45 (s, 1H), 7.39-7.33 (m, 1H), 6.86-6.77 (m, 2H), 5.93-5.86 (brs, 2H), 4.68-4.58 (m, 2H), 4.52-4.47 (m, 1H), 4.28-4.17 (m, 3H), 3.99-3.93 (m, 1H), 3.79-3.75 (m, 1H), 3.52-3.44 (m, 1H), 2.57-2.49 (m, 1H), 1.71-1.58 (m, 1H), 1.50-1.24 (m, 5H), 1.18 (s, 3H). LCMS M+1=521.3.

Example 5

Preparation of Compound 5

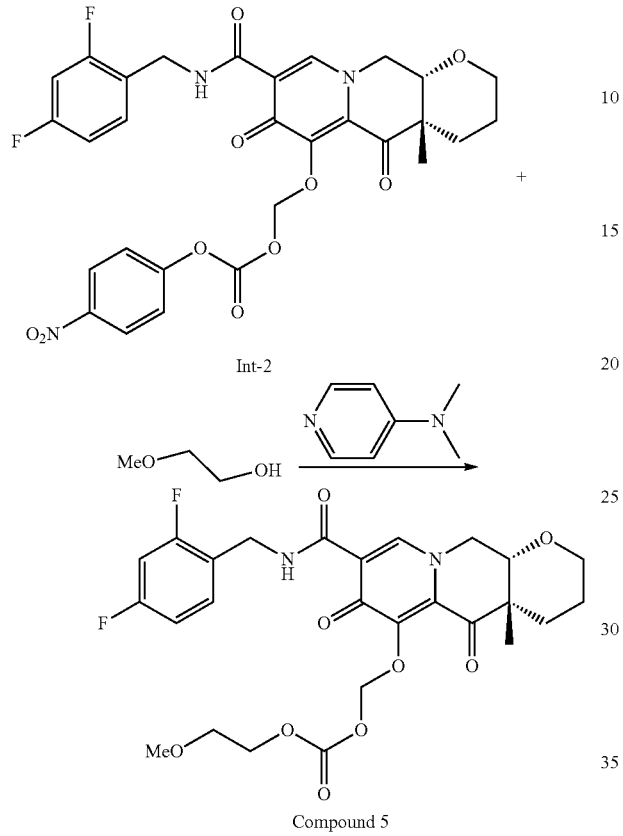

Example 6

Preparation of Compounds 6-9

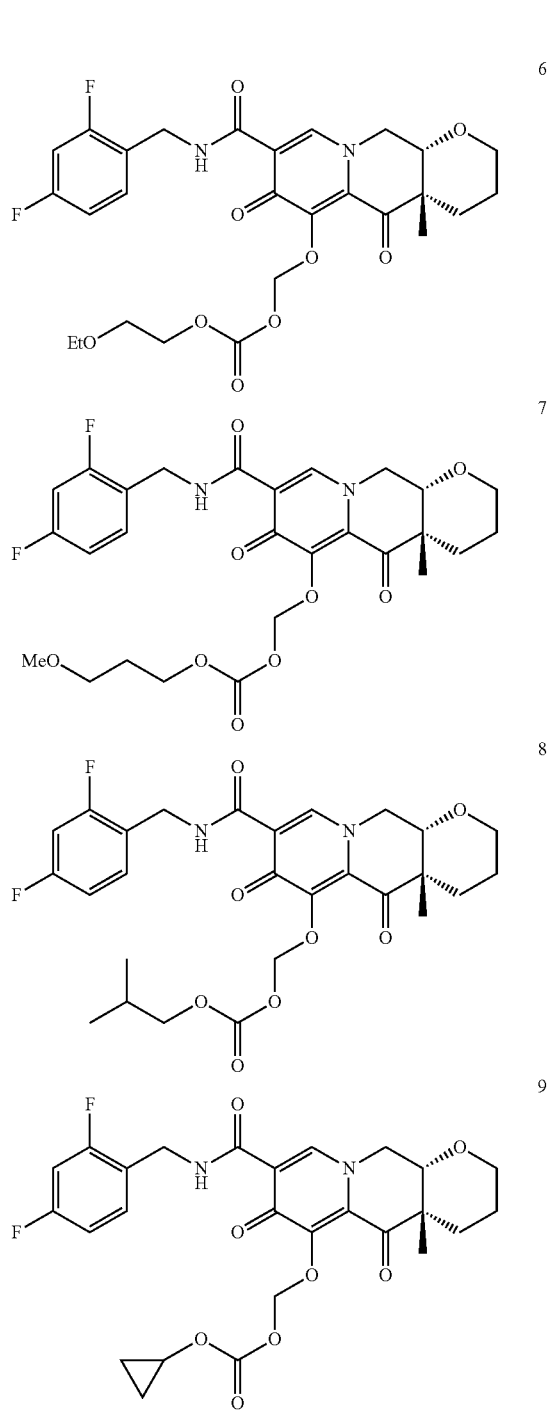

To a solution of compound Int-2 (2 g, 3.26 mmol) in dichloromethane (8.15 ml), was added 2-methoxyethanol (3.86 mL, 48.9 mmol) followed by 4-dimethylaminopyridine (0.040 g, 0.326 mmol). The reaction mixture was stirred at room temperature overnight. The volatile was removed under vacuum. The residue was purified by ISCO, reverse phase HP Gold C18 (150 g), eluting with acetonitrile/water (0% water for 5 min; gradient to 60% acetonitrile in water over 25 min). The product containing fractions were pooled and evaporated under reduced pressure. The residue was diluted with EtOAc and washed with saturated aqueous $NaHCO_3$ solution. The organic layer was washed with brine and concentrated under vacuum. The residue was further purified by ISCO, normal phase HP Gold silica gel (120 g), eluting with dicholromethane/MeOH (100% of dicholromethane for 5 min; gradient to 5% MeOH in dicholromethane over 30 min, isocratic for 10 min) to give compound 5.

Compound 5: $^1$H NMR (400 MHz, $CDCl_3$) δ: 10.34-10.27 (brs, 1H), 8.42 (s, 1H), 7.39-7.33 (m, 1H), 6.86-6.76 (m, 2H), 5.92 (s, 2H), 4.68-4.58 (m, 2H), 4.49 (dd, J=13.6, 2.1 Hz, 1H), 4.37-4.27 (m, 2H), 4.19 (dd, J=13.7, 2.5 Hz, 1H), 3.96 (dd, J=11.2, 4.7 Hz, 1H), 3.79-3.76 (brs, 1H), 3.66-3.60 (m, 2H), 3.52-3.45 (m, 1H), 3.37 (s, 3H), 2.57-2.52 (m, 1H), 1.71-1.60 (m, 1H), 1.50-1.44 (m, 1H), 1.37 (dt, J=13.5, 13.4, 4.3 Hz, 1H), 1.19 (s, 3H). LCMS M+1=551.1.

Following the method employed by Example 5, starting from compound Int-2, compounds 6-9 were prepared, except 2-methoxyethanol was replaced with the corresponding alcohols.

Compound 6: $^1$H NMR (400 MHz, Methanol-$d_4$) δ: 8.53 (s, 1H), 7.44 (td, J=8.5, 6.4 Hz, 1H), 7.01-6.92 (m, 2H), 5.77 (s, 2H), 4.72 (dd, J=14.2, 2.1 Hz, 1H), 4.64 (s, 2H), 4.40 (dd, J=14.2, 2.8 Hz, 1H), 4.25 (td, J=4.3, 2.0 Hz, 2H), 3.94 (dd, J=11.4, 4.6 Hz, 1H), 3.92-3.90 (m, 1H), 3.64 (dd, J=5.4, 4.0 Hz, 2H), 3.57 (dd, J=11.5, 2.2 Hz, 1H), 3.52 (q, J=7.0 Hz, 2H), 2.48-2.41 (m, 1H), 1.60 (dtt, J=20.1, 13.4, 6.5 Hz, 1H), 1.49 (td, J=14.8, 14.0, 4.1 Hz, 2H), 1.22 (s, 3H), 1.18 (t, J=7.0 Hz, 3H). LCMS M+1=565.4.

Compound 7: $^1$H NMR (400 MHz, CDCl$_3$) δ: 10.34-10.26 (brs, 1H), 8.42 (s, 1H), 7.40-7.33 (m, 1H), 6.86-6.76 (m, 2H), 5.92 (d, J=6.5 Hz, 1H), 5.90 (d, J=6.5 Hz, 1H), 4.68-4.58 (m, 2H), 4.49 (dd, J=13.6, 2.0 Hz, 1H), 4.32-4.23 (m, 2H), 4.19 (dd, J=13.7, 2.6 Hz, 1H), 3.96 (dd, J=11.3, 4.6 Hz, 1H), 3.79-3.76 (brs, 1H), 3.52-3.44 (m, 3H), 3.33 (s, 3H), 2.57-2.50 (m, 1H), 1.99-1.91 (m, 2H), 1.70-1.59 (m, 1H), 1.50-1.44 (m, 1H), 1.37 (dt, J=13.4, 13.4, 4.2 Hz, 1H), 1.19 (s, 3H). LCMS M+1=565.1.

Compound 8: $^1$H NMR (400 MHz, CDCl$_3$) δ: 10.33-10.23 (brs, 1H), 8.44 (s, 1H), 7.35-7.24 (m, 1H), 6.80-6.69 (m, 2H), 5.85 (d, J=6.5 Hz, 1H), 5.83 (d, J=6.5 Hz, 1H), 4.61-4.51 (m, 2H), 4.47 (d, J=13.6 Hz, 1H), 4.22 (dd, J=13.8, 2.1 Hz, 1H), 3.95-3.84 (m, 3H), 3.72-3.69 (brs, 1H), 3.46-3.37 (m, 1H), 2.50-2.41 (m, 1H), 1.98-1.86 (m, 1H), 1.63-1.50 (m, 1H), 1.44-1.28 (m, 2H), 1.12 (s, 3H), 0.89 (d, J=6.8 Hz, 6H). LCMS M+1=549.4.

Compound 9: $^1$H NMR (500 MHz, Methanol-d$_4$) δ 8.52 (s, 1H), 7.44 (td, J=8.5, 6.5 Hz, 1H), 7.01-6.92 (m, 2H), 5.79-5.71 (m, 2H), 4.72 (dd, J=14.1, 2.0 Hz, 1H), 4.68-4.59 (m, 2H), 4.40 (dd, J=14.2, 2.7 Hz, 1H), 4.10-4.05 (m, 1H), 3.97-3.90 (m, 2H), 3.55 (td, J=12.1, 11.7, 2.1 Hz, 1H), 2.47-2.40 (m, 1H), 1.65-1.43 (m, 3H), 1.21 (s, 3H), 0.78-0.67 (m, 4H). LCMS M+1=533.27.

Example 7

Preparation of Compound 10 and Compound 11

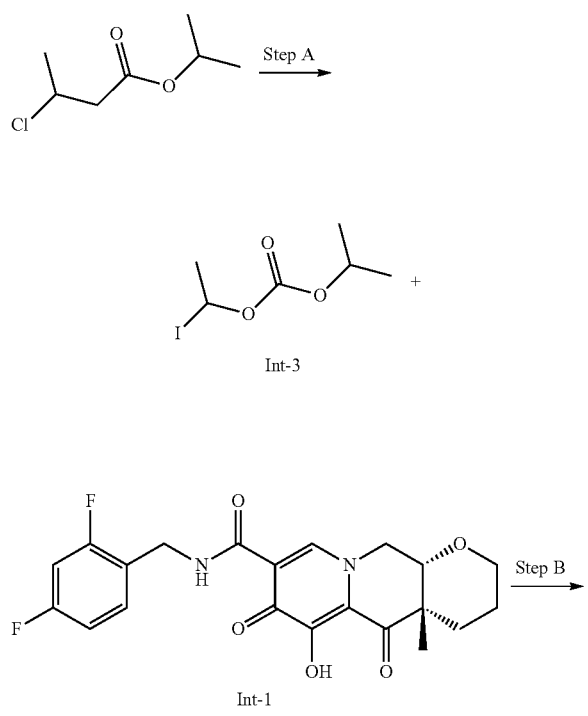

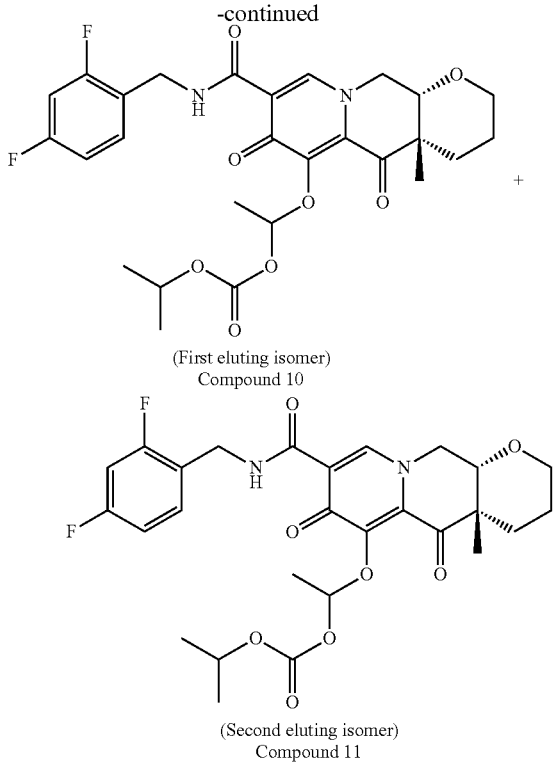

(First eluting isomer)
Compound 10

(Second eluting isomer)
Compound 11

Step A—Synthesis of Compound Int-3

Sodium iodide (4.50 g, 30.0 mmol) was added to a stirred solution of 1-chloroethyl isopropyl carbonate (1.0 ml, 6.69 mmol) in acetonitrile (11.0 mL). The reaction mixture was heated at 60° C. for 3.5 h. The reaction mixture was cooled to room temperature before being filtered. The filtrate was concentrated under reduced pressure, and the residue was partitioned between ethyl acetate (100 mL) and saturated aqueous sodium thiosulfate (50 mL). The organic layer was washed with saturated aqueous sodium thiosulfate (50 mL) and brine (20 mL), dried over MgSO$_4$, filtered, and evaporated under reduced pressure to give compound Int-3. This material was used in the next reaction without further purification. $^1$H NMR (500 MHz, CDCl$_3$) δ 6.77 (q, J=6.1 Hz, 1H), 4.96 (hept, J=6.3 Hz, 1H), 2.25 (d, J=6.1 Hz, 3H), 1.35 (d, J=6.3 Hz, 3H), 1.33 (d, J=6.3 Hz, 3H).

Step B—Synthesis of Compound 10 and Compound 11

Potassium carbonate (121.7 mg, 0.881 mmol) was added to a stirred suspension of compound Int-1 (99.1 mg, 0.237 mmol) and compound Int-3 (176.1 mg, 0.682 mmol) in acetonitrile (2.0 mL). The reaction mixture was heated to 50° C. and stirred for 2 h. The reaction mixture was cooled to room temperature before being filtered, and the cake was rinsed with dichloromethane (20 mL). The filtrate was concentrated under reduced pressure to give an amber residue, which was suspended in MeOH and filtered (0.45 m syringe filter) before being purified on a Waters Sunfire C18, 30×150 mm column, eluting with acetonitrile/water+0.05% TFA at 20 mL/min using a 15 min 20-100% acetonitrile/water gradient. The first eluting fraction was concentrated, and the residue was further purified by a 250 micron 20 cm×20 cm silica gel plate eluting with 5% MeOH/dichloromethane to give compound 10. The second eluting fraction was also concentrated, and the residue was further purified by a 250 micron 20 cm×20 cm silica gel plate eluting with 5% MeOH/dichloromethane to give compound 11.

Compound 10: ¹H NMR (500 MHz, Methanol-d₄) δ 8.50 (s, 1H), 7.44 (td, J=8.5, 6.3 Hz, 1H), 7.01-6.92 (m, 2H), 6.39 (q, J=5.2 Hz, 1H), 4.71 (dd, J=14.1, 1.9 Hz, 1H), 4.68-4.57 (m, 3H), 4.38 (dd, J=14.0, 2.9 Hz, 1H), 3.95-3.89 (m, 2H), 3.55 (dd, J=12.2, 9.9 Hz, 1H), 2.50-2.42 (m, 1H), 1.73 (d, J=5.2 Hz, 3H), 1.65-1.44 (m, 3H), 1.23 (s, 3H), 1.16 (d, J=6.3 Hz, 3H), 1.10 (d, J=6.3 Hz, 3H). LCMS M+1=549.39

Compound 11: ¹H NMR (500 MHz, Methanol-d₄) δ 8.49 (s, 1H), 7.44 (td, J=8.5, 6.3 Hz, 1H), 7.02-6.92 (m, 2H), 6.36 (q, J=5.2 Hz, 1H), 4.71 (dd, J=14.2, 2.3 Hz, 1H), 4.68-4.58 (m, 3H), 4.39 (dd, J=14.3, 2.7 Hz, 1H), 3.95 (dd, J=11.4, 4.8 Hz, 1H), 3.91 (t, J=2.3 Hz, 1H), 3.56 (td, J=11.8, 2.3 Hz, 1H), 2.48-2.41 (m, 1H), 1.74 (d, J=5.3 Hz, 3H), 1.66-1.44 (m, 3H), 1.19 (s, 3H), 1.18 (d, J=6.9 Hz, 3H), 1.14 (d, J=6.2 Hz, 3H). LCMS M+1=549.41

Example 8

Preparation of Compound 12

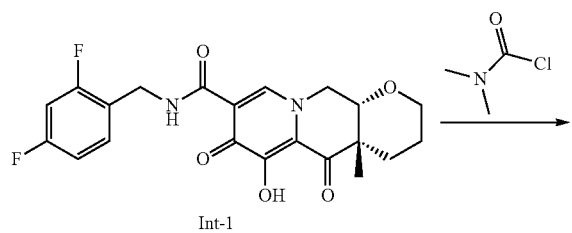

Int-1

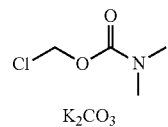

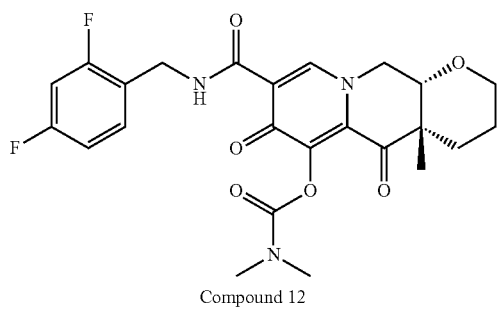

Compound 12

A solution of compound Int-1 (100 mg, 0.239 mmol) in pyridine (1195 μl) was treated with dimethylcarbamic chloride (66.0 μl, 0.717 mmol). The solution was heated to 80° C. and stirred overnight. The mixture was concentrated and the crude material was purified by ISCO, normal phase HP Gold silica gel (12 g), eluting with dichloromethane/MeOH (0 to 10% MeOH in dichloromethane over 15 min) to provide compound 12.

Compound 12: ¹H NMR (500 MHz, DMSO-d₆) δ 10.24 (t, J=5.9 Hz, 1H), 8.61 (s, 1H), 7.39 (td, J=8.6, 6.5 Hz, 1H), 7.23 (td, J=9.9, 2.6 Hz, 1H), 7.05 (td, J=8.6, 2.6 Hz, 1H), 4.79-4.59 (m, 1H), 4.54 (m, 3H), 3.92 (m, 1H), 3.83 (d, J=11.2 Hz, 1H), 3.45 (dt, J=12.5, 6.0 Hz, 1H), 3.02 (s, 3H), 2.88 (s, 3H), 2.25 (d, J=12.5 Hz, 1H), 1.45-1.25 (m, 3H), 1.13 (s, 3H). LCMS M+1=490.3.

Example 9

Preparation of Compound 13

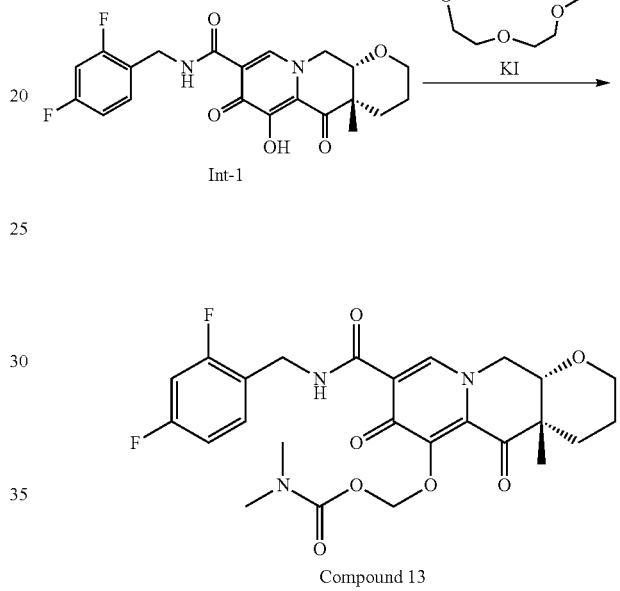

Compound 13

A solution of compound Int-1 (100 mg, 0.239 mmol) in 1.2 mL of acetonitrile, was treated with potassium carbonate (99 mg, 0.717 mmol), potassium iodide (119 mg, 0.717 mmol), 18-crown-6 (3.16 mg, 0.012 mmol) followed by chloromethyl dimethylcarbamate (65.8 mg, 0.478 mmol). The reaction mixture was stirred at 80° C. for 16 h. The resulting mixture was cooled to room temperature, and partitioned between ethyl acetate and water. The aqueous phase was back extracted with ethyl acetate and the combined organic layers were dried over Na₂SO₄, filtered, and concentrated in vacuo. The residue was purified on a XBridge™ C18, 30×250 mm column, eluting with acetonitrile/water (5 mM NH₄HCO₃) at 50 mL/min using a 20 min 20-90% acetonitrile/water gradient. Clean fractions were partitioned between water and dichloromethane. The organic phase was dried over Na₂SO₄, filtered and concentrated to give compound 13.

Compound 13: ¹H NMR (500 MHz, Chloroform-d) δ 10.36 (t, J=5.9 Hz, 1H), 8.38 (s, 1H), 7.35 (td, J=8.4, 6.4 Hz, 1H), 6.89-6.68 (m, 2H), 5.91 (d, J=6.3 Hz, 1H), 5.85 (d, J=6.3 Hz, 1H), 4.67-4.55 (m, 2H), 4.48 (dd, J=13.7, 2.3 Hz, 1H), 4.18 (dd, J=13.7, 2.5 Hz, 1H), 3.95 (dd, J=11.4, 4.8 Hz, 1H), 3.75 (m, 1H), 3.47 (ddd, J=13.1, 11.5, 2.5 Hz, 1H), 2.92 (s, 3H), 2.85 (s, 3H), 2.59-2.45 (m, 1H), 1.63 (m, 1H), 1.49-1.40 (m, 1H), 1.34 (td, J=13.4, 4.4 Hz, 1H), 1.17 (s, 3H). LCMS M+1=520.3.

Example 10

Preparation of Compound 14

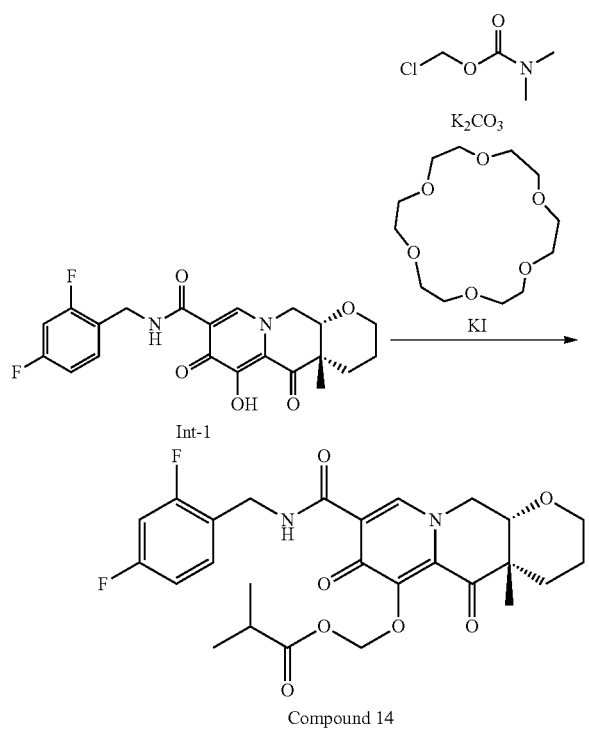

Int-1

Compound 14

A solution of compound Int-1 (100 mg, 0.239 mmol) in 1.2 mL of acetonitrile, was treated with potassium carbonate (99 mg, 0.717 mmol), potassium iodide (119 mg, 0.717 mmol), 18-crown-6 (3.16 mg, 0.012 mmol) followed by chloromethyl isobutyrate (65.3 mg, 0.478 mmol). The reaction mixture was stirred at 80° C. for 16 h. The resulting mixture was cooled to room temperature, and partitioned between ethyl acetate and water. The aqueous phase was back extracted with ethyl acetate and the combined organic layers were dried over $Na_2SO_4$, filtered, and concentrated in vacuo. The residue was purified on a XBridge™ C18, 30×250 mm column, eluting with acetonitrile/water (5 mM $NH_4HCO_3$) at 50 mL/min using a 20 min 20-90% acetonitrile/water gradient. Clean fractions were partitioned between water and dichloromethane. The organic phase was dried over $Na_2SO_4$, filtered and concentrated to give compound 14.

Compound 14: $^1$H NMR (500 MHz, DMSO-$d_6$) δ 10.30 (t, J=5.9 Hz, 1H), 8.55 (s, 1H), 7.40 (td, J=8.7, 6.6 Hz, 1H), 7.23 (td, J=10.0, 2.6 Hz, 1H), 7.05 (td, J=8.6, 2.5 Hz, 1H), 5.84-5.61 (m, 2H), 4.63 (dd, J=14.4, 2.2 Hz, 1H), 4.58-4.46 (m, 3H), 3.89 (m, 1H), 3.87-3.76 (m, 1H), 3.44 (m, 1H), 2.45 (m, 1H), 2.23 (d, J=10.2 Hz, 1H), 1.48-1.30 (m, 3H), 1.11 (s, 3H), 1.04 (d, J=7.0 Hz, 6H). LCMS M+1=519.3.

Biological Assays

Stability of Compounds in Blood

Selected compounds of the present invention (1 μM) were incubated with whole blood (with heparin) from rat, dog and human. The samples were incubated for 0, 0.5, 1 and 2 hours in a 95% humidified incubator at 37° C. with 5% $CO_2$. At each time point, the samples were quenched with acetonitrile containing an appropriate internal standard. The samples were then vortex-mixed and centrifuged at 2,500×g for 20 minutes. The supernatants were transferred to clean plates and analyzed using LC-MS/MS. The stability of the analyte was assessed by determining the percentage of drug loss over the course of time.

Prodrug Hydrolysis in Hepatocyte Suspensions

| Compound | Remaining at 2 hours | | |
|---|---|---|---|
| | Rat | Dog | Human |
| 1 | 0% | 19% | 24% |

Dog Pharmacokinetic Studies

Male Beagle Dogs (Marshall Farms) were used for the pharmacokinetic studies. Studies were conducted under a protocol approved by the WP-IACUC (Animal Procedure Statement #2018-600787-MAR). Following overnight-fasting, dogs were dosed orally with either Compound Int-1 at 10 mg/kg or one of the respective prodrugs at the dose equivalent to 10 mg/kg of Compound Int-1 formulated as a suspension in Orablend® SF. Dosing was followed by 15 mL water rinse via oral gavage. Food was returned at 4 hours after dosing. Blood (0.5-mL) was drawn at pre-dose, 0.25, 0.5, 1, 2, 4, 6, 24, 30, 48, 54 and 72 hours post-dosing into EDTA-coated collection tubes containing 25 μL of 2 mM dichlorvos solution in water. The tubes were kept chilled prior to blood collection and throughout plasma separation. The plasma was separated by centrifugation (2 minutes at 10000 g). After processing, 10 uL of 10% formic acid was added to each 200 uL of plasma. Acidified plasma samples were immediately frozen and kept at −70° C. until analysis by LC-MS/MS.

Mean [±SD] Pharmacokinetic Parameters for Compounds after Oral Administration to Fasted Beagle Dogs at Dose Equivalent to 10 mg/kg of Compound Int-1.

| Compound Dosed | Dosing Route | Compound Measured | AUC0-72 hr (μM · hr) | Cmax (μM) |
|---|---|---|---|---|
| Int-1 | Oral | Int-1 | 1033 ± 357 | 30 ± 4 |
| 1 | Oral | Int-1 | 998 ± 260 | 42 ± 8 |
| 2 | Oral | Int-1 | 1414 ± 91 | 52 ± 1 |
| 3 | Oral | Int-1 | 3003 ± 397 | 132 ± 11 |
| 4 | Oral | Int-1 | 2633 ± 51 | 184 ± 28 |
| 5 | Oral | Int-1 | 1182 ± 322 | 48 ± 3 |
| 6 | Oral | Int-1 | — | — |
| 7 | Oral | Int-1 | 1341 ± 69 | 56 ± 3 |
| 8 | Oral | Int-1 | 1317 ± 88 | 91 ± 9 |
| 9 | Oral | Int-1 | — | — |
| 10 | Oral | Int-1 | — | — |
| 11 | Oral | Int-1 | — | — |
| 12 | Oral | Int-1 | — | — |
| 13 | Oral | Int-1 | — | — |
| 14 | Oral | Int-1 | — | — |

As shown above, Compounds 3 and 4, which are representative compounds of the present invention, show significant increase in absorption versus their metabolite, Compound Int-1.

What is claimed is:

1. A compound having the formula (I):

[Structure of Formula (I)]

wherein:
R¹ is X—C(O)—Y—R²;
X is O—(C₁-C₆ alkylene)-O or O; and
Y is a bond, O or NR³;
R² is selected from $C_1$-$C_6$ alkyl or $C_3$-$C_6$ cycloalkyl, wherein said $C_1$-$C_6$ alkyl group can be optionally substituted with one to three groups independently selected from the group consisting of halo, hydroxy, methoxy and ethoxy;
R³ is selected from hydrogen or $C_1$-$C_6$ alkyl;
or a pharmaceutically acceptable salt thereof.

2. The compound of claim 1, wherein X is O, or a pharmaceutically acceptable salt thereof.

3. The compound of claim 1, wherein X is O—($C_1$-$C_6$ alkylene)-O, or a pharmaceutically acceptable salt thereof.

4. The compound of claim 1, wherein Y is O, or a pharmaceutically acceptable salt thereof.

5. The compound of claim 1, wherein Y is a bond, or a pharmaceutically acceptable salt thereof.

6. The compound of claim 1, wherein Y is NR³, or a pharmaceutically acceptable salt thereof.

7. The compound of claim 1, wherein R² is selected from the group consisting of methyl; ethyl, which is optionally substituted with methoxy or ethoxy; propyl, which is optionally substituted with methoxy; or cyclopropyl; or a pharmaceutically acceptable salt thereof.

8. The compound of claim 1, wherein R¹ is selected from:

[Structures]

or a pharmaceutically acceptable salt thereof.

9. The compound of claim 1, wherein R¹ is

[Structure]

or a pharmaceutically acceptable salt thereof.

10. The compound of claim 1 having the structure

[Structure]

35
-continued
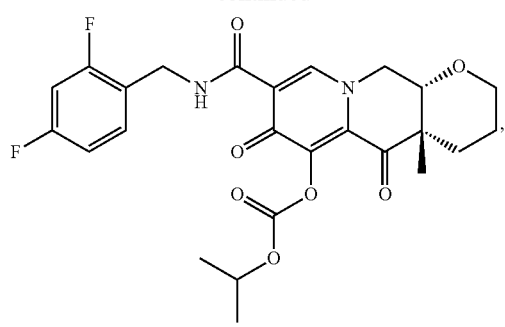
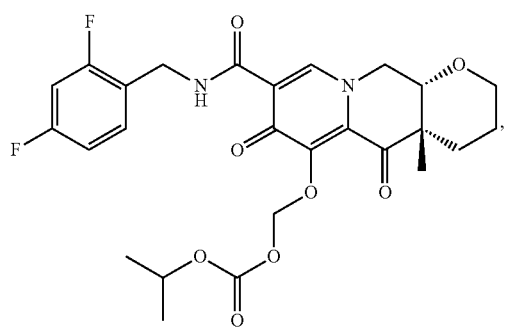
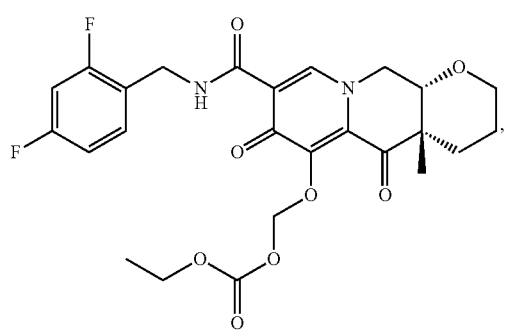
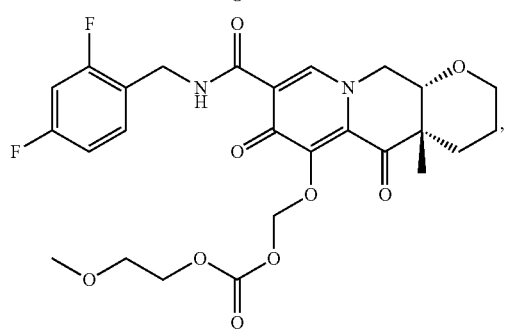
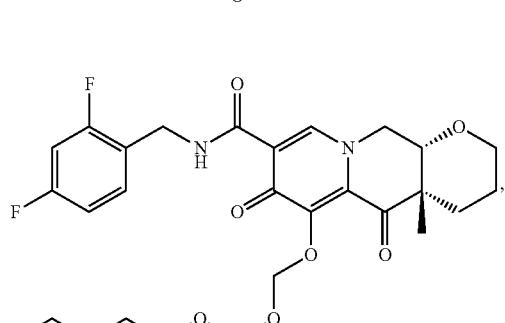
36
-continued
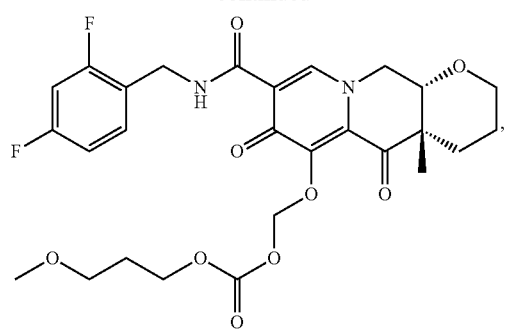
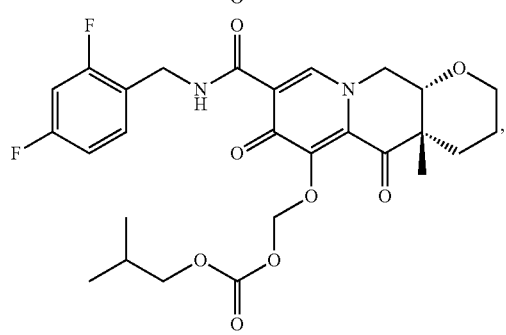
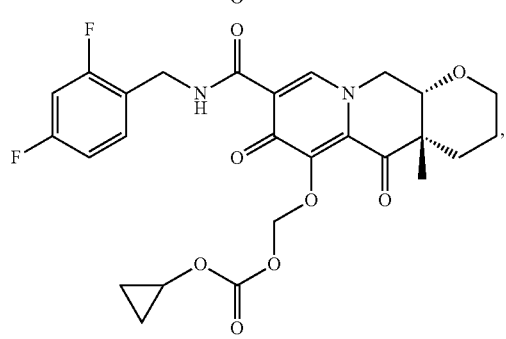
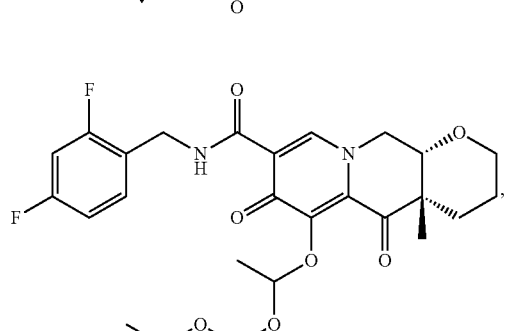
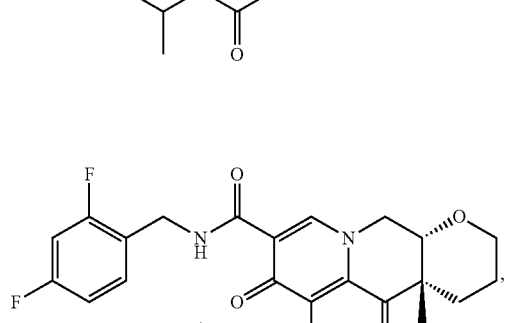

-continued

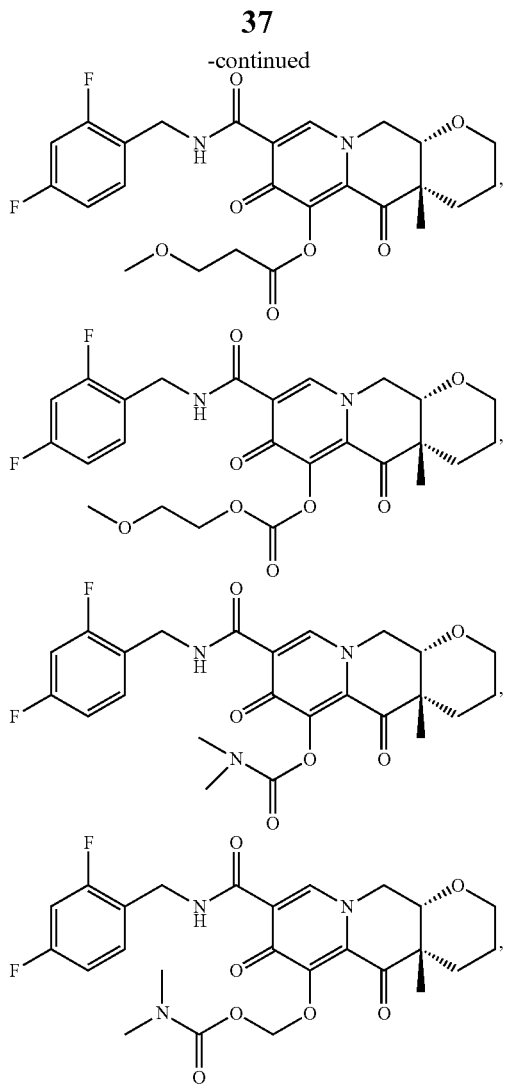

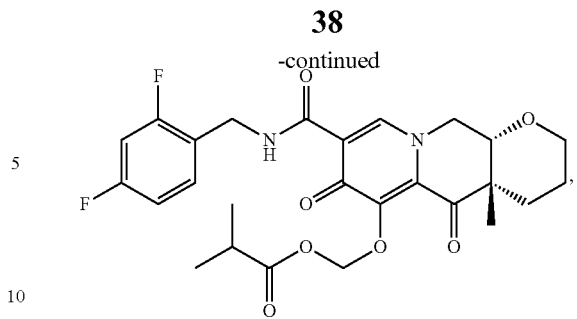

or a pharmaceutically acceptable salt thereof.

11. A pharmaceutical composition comprising an effective amount of a compound according to claim 1, or a pharmaceutically acceptable salt thereof, and a pharmaceutically acceptable carrier.

12. A method for the inhibition of HIV integrase in a subject in need thereof which comprises administering to the subject an effective amount of the compound according to claim 1, or a pharmaceutically acceptable salt thereof.

13. A method for the treatment of infection by HIV or for the treatment of AIDS or delay the onset of AIDS in a subject in need thereof, which comprises administering to the subject an effective amount of the compound according to claim 1, or a pharmaceutically acceptable salt thereof.

14. The composition of claim 11, further comprising one or more additional therapeutic agents selected from raltegravir, lamivudine, abacavir, ritonavir, dolutegravir, arunavir, atazanavir, emtricitabine, tenofovir, elvitegravir, rilpivirine and lopinavir.

15. The method of claim 13, further comprising administering to the subject one or more additional therapeutic agents selected from raltegravir, abacavir, lamivudine, ritonavir and lopinavir, wherein the amounts administered of the compound of claim 1 and the one or more additional therapeutic agents, are together effective to treat infection by HIV or to treat AIDS or delay the onset of AIDS.

* * * * *